United States Patent
Itoh et al.

(10) Patent No.: US 9,194,825 B2
(45) Date of Patent: Nov. 24, 2015

(54) IMAGING APPARATUS USING TALBOT INTERFERENCE AND ADJUSTING METHOD FOR IMAGING APPARATUS

(71) Applicant: CANON KABUSHIKI KAISHA, Tokyo (JP)

(72) Inventors: Hidenosuke Itoh, Tokyo (JP); Kentaro Nagai, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/643,996

(22) Filed: Mar. 10, 2015

(65) Prior Publication Data

US 2015/0185169 A1  Jul. 2, 2015

Related U.S. Application Data

(63) Continuation of application No. 13/824,974, filed as application No. PCT/JP2011/073773 on Oct. 11, 2011, now Pat. No. 9,006,656.

(30) Foreign Application Priority Data

Oct. 20, 2010  (JP) .................................. 2010-235490
Aug. 8, 2011  (JP) .................................. 2011-172973

(51) Int. Cl.
| | |
|---|---|
| *G01J 1/00* | (2006.01) |
| *G01N 23/20* | (2006.01) |
| *G01N 23/04* | (2006.01) |
| *G21K 1/06* | (2006.01) |
| *G01B 9/02* | (2006.01) |

(52) U.S. Cl.
CPC ...... *G01N 23/20075* (2013.01); *G01B 9/02068* (2013.01); *G01N 23/04* (2013.01); *G21K 1/06* (2013.01); *G21K 2207/005* (2013.01)

(58) Field of Classification Search
CPC ............................ G01T 1/17; G01N 23/20075
See application file for complete search history.

(56) References Cited

U.S. PATENT DOCUMENTS

2012/0099702 A1* 4/2012 Engel et al. ..................... 378/62

FOREIGN PATENT DOCUMENTS

| | | |
|---|---|---|
| JP | H02-188907 A | 7/1990 |
| JP | 2010-190777 A | 9/2010 |
| WO | 2010/050483 A1 | 5/2010 |

* cited by examiner

*Primary Examiner* — David Porta
*Assistant Examiner* — Hugh H Maupin
(74) *Attorney, Agent, or Firm* — Canon USA Inc. IP Division

(57) ABSTRACT

An imaging apparatus includes a diffraction grating which diffracts electromagnetic waves from an electromagnetic wave source, a shield grating which shields a part of the electromagnetic waves diffracted by the diffraction grating, a detector which detects an intensity distribution of the electromagnetic waves through the shield grating, and an adjusting unit which adjusts the attitude of at least one of the diffraction grating and the shield grating on the basis of the detection result by the detector, wherein the adjusting unit divides the intensity distribution detected by the detector into a plurality of regions and adjusts the attitude of at least one of the diffraction grating and the shield grating on the basis of the intensity distributions of the plurality of regions.

8 Claims, 8 Drawing Sheets

IMAGING APPARATUS USING TALBOT INTERFERENCE AND ADJUSTING METHOD FOR IMAGING APPARATUS

CROSS-REFERENCE TO RELATED APPLICATIONS

This application is a Continuation of co-pending U.S. patent application Ser. No. 13/824,974, filed Mar. 18, 2013, which is a U.S. national stage application of International Patent Application No. PCT/JP2011/073773, filed Oct. 11, 2011, which claims foreign priority benefit to Japanese Patent Applications No. 2010-235490, filed Oct. 20, 2010 and No. 2011-172973, filed Aug. 8, 2011. All of the above-listed applications are hereby incorporated by reference herein in their entirety.

TECHNICAL FIELD

The present invention relates to imaging apparatus using Talbot interference and adjusting methods for an imaging apparatus.

BACKGROUND ART

Talbot interference uses an interference of electromagnetic waves having various wavelengths including light or an X-ray to measure a form or composition of a subject. Generally, Talbot interference uses an imaging apparatus including an electromagnetic wave source, a diffraction grating, and a detector. The principle of Talbot interference will be described briefly. First of all, incident waves having a phase wavefront, that is, coherent incident waves are irradiated from an electromagnetic source to a subject. The electromagnetic waves through the subject changes their wavefront in accordance with the form or composition of the subject. When the electromagnetic waves having the wavefront change are diffracted by a diffraction grating, an interference pattern is formed at a position away from the diffraction grating by a specific distance called a Talbot distance. The interference pattern is detected and analyzed by a detector so that the phase wavefront (hereinafter, called a phase image) changed by the subject or the differential image of the phase wavefronts (hereinafter, called a differential image) may be acquired.

As disclosed in PTL 1, a shield grating (hereafter, called absorption grating) having a transmitting unit which allows electromagnetic waves to pass through and a shielding unit which shields electromagnetic waves at predetermined periods may be placed at a position where an interference pattern occurs to form a moire. The moire may be detected and analyzed to acquire the phase image or differential image of the subject. According to this method, a detector may be used which has a larger spatial resolution than the period of the interference pattern. For that reason, the method is often used in imaging apparatus according to Talbot interference using an X-ray as the electromagnetic waves (hereinafter, called an X-ray Talbot interference).

In a Talbot interferometer which uses an absorption grating to form a moire and detects the intensity distribution of the moire, the attitude of the diffraction grating or the absorption grating suitable for imaging depends on the wavelength of the electromagnetic waves to be used or the pitch of the diffraction grating or absorption grating. When the attitude of the diffraction grating or absorption grating is displaced from the attitude suitable for imaging, the noise ratio to the acquired phase image or differential image of the subject increases, which then may deteriorate the image quality.

CITATION LIST

Patent Literature

PTL 1 Japanese Patent Laid-Open No. 2010-164373

SUMMARY OF INVENTION

The present invention provides an imaging apparatus which adjusts the attitude of the diffraction grating or absorption grating to an attitude suitable for imaging apparatus to acquire a high-quality phase image or differential image.

Solution to Problem

According to an aspect of the present invention, there is provided an imaging apparatus including a diffraction grating which diffracts electromagnetic waves from an electromagnetic wave source, an absorption grating which absorbs a part of the electromagnetic waves diffracted by the diffraction grating, a detector which detects an intensity distribution of the electromagnetic waves through the absorption grating, and an adjusting unit which adjusts the attitude of at least one of the diffraction grating and the absorption grating on the basis of the detection result by the detector, wherein the adjusting unit divides the intensity distribution detected by the detector into a plurality of regions and adjusts the attitude of at least one of the diffraction grating and the absorption grating on the basis of the intensity distributions of the plurality of regions.

Other aspects of the present invention will be clarified in the descriptions on embodiments below.

Advantageous Effects of Invention

According to the present invention, an imaging apparatus may be provided which adjusts the attitude of at least one of a diffraction grating and an absorption grating therein to acquire a phase image or differential image having higher image quality.

DESCRIPTION OF EMBODIMENTS

Figure 1:
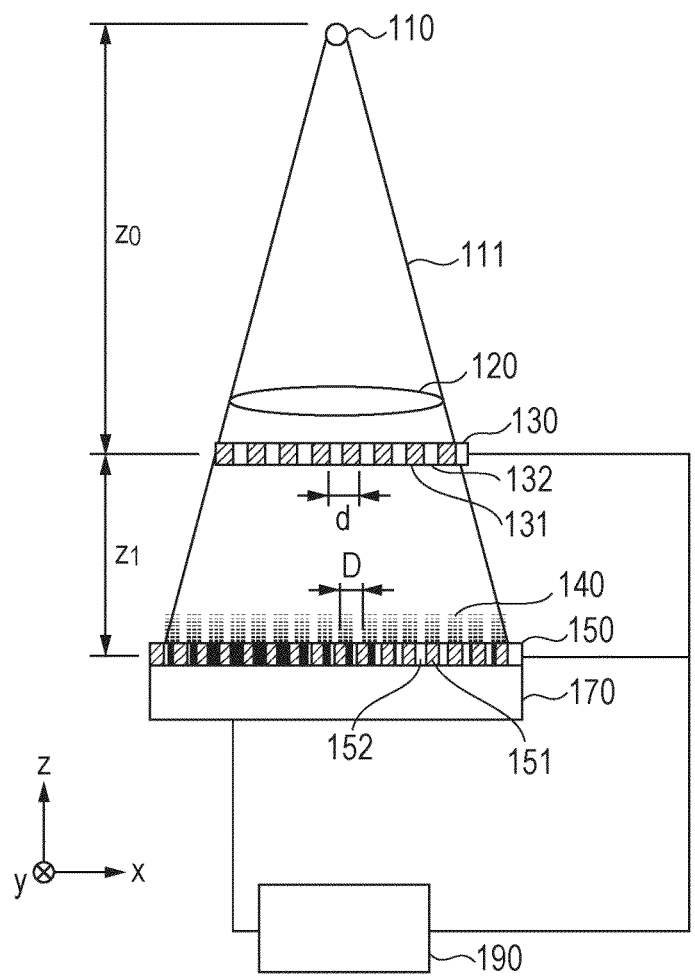
FIG. 1 illustrates an X-ray imaging apparatus according to an embodiment of the present invention.

Hereinafter, embodiments of the present invention will be described in detail with reference to the attached drawings. In the drawings, like numbers refer to like members, and repetitive descriptions will be omitted. Hereinafter, an X-ray imaging apparatus using X-ray Talbot interference will be described according to first and second embodiments, for example. An imaging apparatus according to first and second embodiments divides the intensity distribution (moire) detected by a detector into a plurality of regions and adjusts the attitude of at least one of a diffraction grating and a absorption grating on the basis of the intensity distributions of the regions. More specifically, Fourier transform is first performed on each of the divided regions to acquire the intensity information on the spectra corresponding to the carrier frequencies. Next, on the basis of the intensity information on the spectra corresponding to the carrier frequencies of the regions, the attitude of at least one of a diffraction grating and absorption grating is adjusted. More specific embodiments will be described below.

First Embodiment

According to this embodiment, for each of the plurality of divided regions, a Carrier to Noise Ratio (hereinafter, called a CNR) is calculated which is the ratio of the peak intensity of the spectrum corresponding to the carrier frequency and the intensity of background noise around the spectrum. On the basis of the calculated CNR value, the attitude of at least one of a diffraction grating and an absorption grating is adjusted.

FIG. 1 illustrates an example of a configuration of this embodiment. The X-ray imaging apparatus illustrated in FIG. 1 includes an X-ray source 110, a diffraction grating 130 which diffracts an X-ray from the X-ray source, an absorption grating 150 which absorbs a part of the X-ray diffracted by the diffraction grating 130, and a detector 170 which detects an X-ray passed through the absorption grating. The X-ray imaging apparatus further includes an adjusting unit 190 which adjusts the attitudes of the diffraction grating 130 and absorption grating 150. The imaging apparatus captures the phase information of a subject 120 as a moire. These components will be described below.

X-Ray Source

The imaging apparatus according to this embodiment includes an X-ray source as an electromagnetic wave source. When an X-ray 111 generated by the X-ray source 110 passes through a subject 120, the X-ray 111 may be changed in phase and be absorbed in accordance with the composition and form of the subject 120.

The X-ray source may generate continuous X-rays or a characteristic X-ray. One wavelength is selected that is equal to or higher than 0.1 Å and equal to or lower than 5 Å. A radiation source grating or wavelength selecting filter for dividing an X-ray into narrow beams may be provided on the path of the X-ray emitted from the X-ray source 110.

Diffraction Grating

The diffraction grating 130 is a phase grating having the phase progression unit 131 and the phase delay unit 132 at predetermined periods. Though the diffraction grating may be an absorption grating having a shielding unit and a transmitting unit at predetermined periods, a phase grating may produce a more amount of X-ray. The diffraction grating 130 diffracts the X-ray 111 and thus forms an interference pattern 140 having a bright part and a dark part. The part having a high X-ray (electromagnetic wave) intensity is called a bright part, and the part having a low intensity is called a dark part, herein.

Though the diffraction grating 130 is placed between the subject 120 and the absorption grating 150 in FIG. 1, it may be placed between an X-ray source and a subject. When the diffraction grating 130 is placed between the subject 120 and the absorption grating 150, the X-ray changed in phase wavefront by the subject is diffracted, and an interference pattern having the phase information of the subject is thus formed. On the other hand, when a diffraction grating is placed between an X-ray source and a subject, the phase wavefront of the X-ray diffracted by the diffraction grating is changed by the subject, and an interference pattern having the phase information of the subject is thus formed.

The phase progression unit 131 and phase delay unit 132 may be provided such that the transmitted X-rays may have a significant phase difference. In general, the phase difference between the X-ray passed through the phase delay unit 132 and the X-ray through the phase progression unit 131 is equal to $\pi$ or $\pi/2$. The former may be called a $\pi$ diffraction grating, and the latter may be called a $\pi/2$ diffraction grating. However, the phase difference between the X-ray through the phase delay unit 132 and the X-ray through the phase progression unit 131 may not be equal to $\pi$ or $\pi/2$ but may be constant within the region where the X-rays are diffracted. For example, the phase difference between the transmitted X-rays may be $\pi/3$.

Figure 2A:
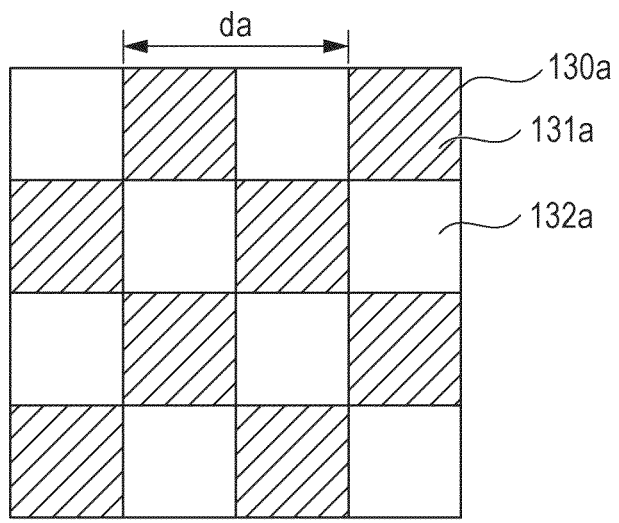
FIG. 2A illustrates a two-dimensional diffraction grating according to an embodiment of the present invention.
Figure 2B:
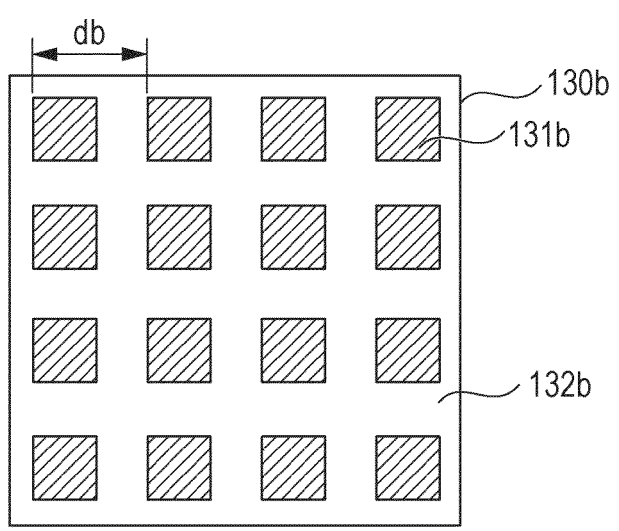
FIG. 2B illustrates a two-dimensional diffraction grating according to an embodiment of the present invention.

The phase progression units 131 and the phase delay units 132 may be arranged to have a one-dimensional period or two-dimensional period. An example of the diffraction grating having the phase progression unit 131 and the phase delay unit 132 at two-dimensional periods therebetween may be a diffraction grating as illustrated in FIG. 2A having phase progression units 131$a$ and phase delay units 132$a$ arranged in a checker grid form. Alternatively, phase progression units 131$b$ and phase delay units 132$b$ may be arranged in a parallel cross pattern, as illustrated in FIG. 2B. However, the arrangement methods and forms of the phase progression units 131 and phase delay units 132 are not limited thereto. For example, phase progression units or phase delay units having round outer edges may be sued as the diffraction grating.

When the diffraction grating 130 has one-dimensional periods, the phase gradient information in the one-dimensional direction on the subject 120 may only be acquired. However, when the diffraction grating 130 has two-dimensional periods, phase gradient information in the two-dimensional direction may be acquired. Thus, more accurate phase information on the subject may be acquired.

The diffraction grating 130 may contain a substance which allows an X-ray to pass through and may contain silicon, for example.

The interference pattern formed by an X-ray diffracted by the diffraction grating 130 appears the most clearly at a position where the distance $Z_1$ from the diffraction grating 130 satisfies the following Expression (1), assuming that the distance between the X-ray source 110 and the diffraction grating 130 is equal to $Z_0$.

In Expression (1), λ is a wavelength of an X-ray, and d is a grating period of the diffraction grating 130.

[Math. 1]

$$\frac{1}{Z_0} + \frac{1}{Z_1} = \frac{1}{N}\frac{\lambda}{d^2} \quad (1)$$

N is a value depending on the form of the diffraction grating and may be a real number which may be expressed as follows:
One-dimensional π diffraction grating: N=n/4−⅛
One-dimensional π/2 diffraction grating: N=n−½
Two-dimensional π diffraction grating with checkers pattern: N=n/4−⅛
Two-dimensional π/2 diffraction grating with checkers pattern: N=n/2−¼
In this case, n is a natural number.

Absorption Grating

The absorption grating 150 has a transmitting unit 151 and a shielding unit 152 periodically and shields a part of an X-ray forming a bright part of the interference pattern 140 to form a moire. In order to do so, the absorption grating 150 is preferably provided at a position away from the diffraction grating 130 by a distance $Z_1$. However, the absorption grating may be displaced by an amount equivalent to a manufacturing error to form a moire. (The interference pattern 140 and the absorption grating 150 are illustrated separately from each other in FIG. 1 for convenience of illustration.)

The shielding units 152 and transmitting units 151 may shield or allow an X-ray to pass through to the degree that a moire appears when the absorption grating is placed at the position where the interference pattern 140 is formed, and the complete shield or transmission of the X-ray may not be required. The transmitting units 151 may be through-holes or may contain a substance such as silicon which allows an X-ray to pass through. On the other hand, the shielding unit 152 may contain gold, for example.

The period of the absorption grating 150 is equal to that of the interference pattern or is slightly different. When a absorption grating having the same period as that of the interference pattern is used, the absorption grating is in-plane rotated about the interference pattern to generate a moire. The period Dm of a moire is equal to D/θ where the period of the interference pattern is D, and the angle formed by the direction of the period of the bright and dark parts of the interference pattern and the direction of period of the absorption grating is θ (θ<<1 radian).

On the other hand, when an absorption grating having a slightly different period from that of the interference pattern, a moire is generated without the in-plane rotation of the absorption grating. The period Dm of the moire is D2/δ where the period of the absorption grating Da is equal to D+δ (δ<<D).

In the absorption grating 150, the transmitting units 151 and the shielding units 152 may be arranged one-dimensionally periodically or two-dimensionally periodically.

Figure 3A:
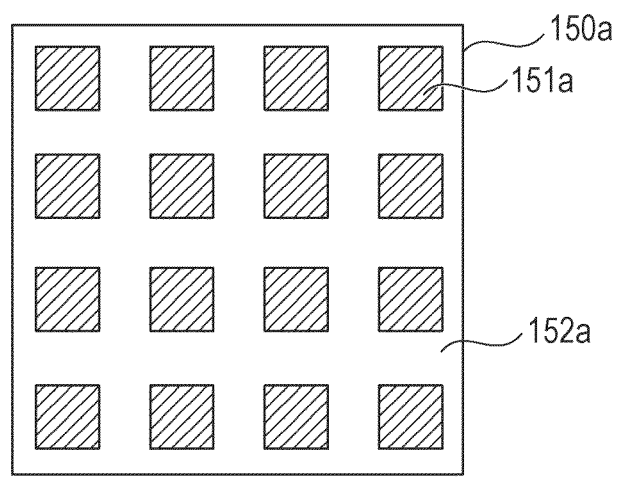
FIG. 3A illustrates a two-dimensional absorption grating according to an embodiment of the present invention.
Figure 3B:
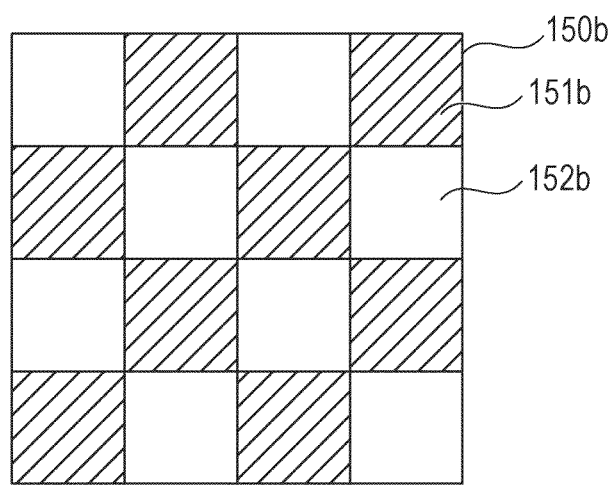
FIG. 3B illustrates a two-dimensional absorption grating according to an embodiment of the present invention.

For example, a diffraction grating is used which has a checker grid form illustrated in FIG. 2A and is a π diffraction grating, the transmitting units 151a and shielding units 152a are two-dimensionally arranged as illustrated in FIG. 3A to form an absorption grating 150a having a parallel cross pattern. When a π/2 diffraction grating having the checker grid form illustrated in FIG. 2A, an absorption grating 150b may be used which has a checker grid form where transmitting units 151b and shielding units 152b are two-dimensionally arranged as illustrated in FIG. 3B.

These combinations are given for illustration purpose only, and the diffraction grating and absorption grating may be combined variously.

Detector

The information on an interference pattern of an X-ray passed through the absorption grating 150 is detected by the X-ray detector 170 as an intensity distribution of a moire. The X-ray detector 170 is an imaging element which can capture a moire of an X-ray. The detector may be an FPD (Flat Panel Detector), for example, which is capable of converting to a digital signal.

Adjusting Unit

Figure 4:
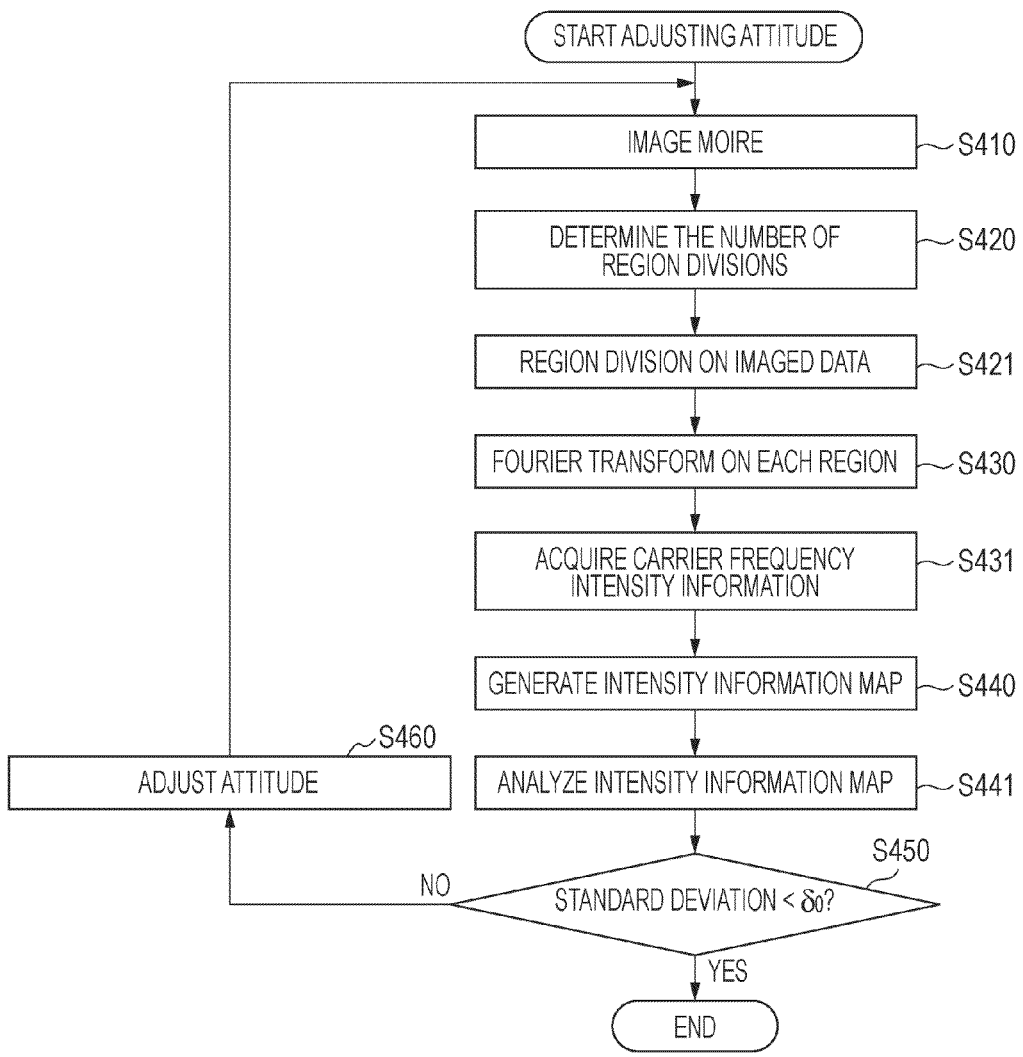
FIG. 4 illustrates an adjustment flow in an adjusting unit according to an embodiment of the present invention.

The adjusting unit 190 divides an intensity distribution of a moire picked up by the detector into a plurality of regions, calculates spectrum intensity information corresponding to the carrier frequencies of the regions, and adjusts the attitude of the absorption grating or diffraction grating on the basis of the distribution of the intensity information. However, the carrier frequency herein refers to the frequency of the regular interval component of a moire. How the attitude of the diffraction grating and absorption grating is to be performed by the adjusting unit will be described with reference to FIG. 4.

In step S410, a moire is captured to acquire the intensity distribution of the moire as the intensity data of pixels on the detector.

In step S420, the number of region divisions is determined. The number of region divisions is determined on the basis of the precision of the grating adjustment and/or the distribution condition of spectrum intensity information corresponding to the carrier frequencies. However, the number of region divisions may be predetermined on the basis of the precision of grating adjustment, without consideration of the distribution condition of the spectrum intensity information corresponding to the carrier frequencies, and the predetermined number of region divisions may be used for the attitude adjustment. In that case, step S420 is not performed.

Figure 5A:
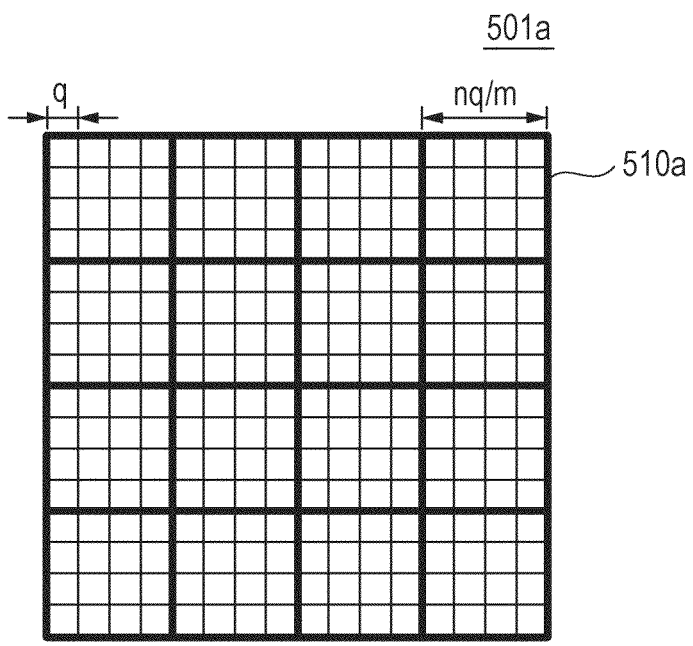
FIG. 5A illustrates a region division method example for the intensity distribution of a moire according to an embodiment of the present invention.
Figure 5B:
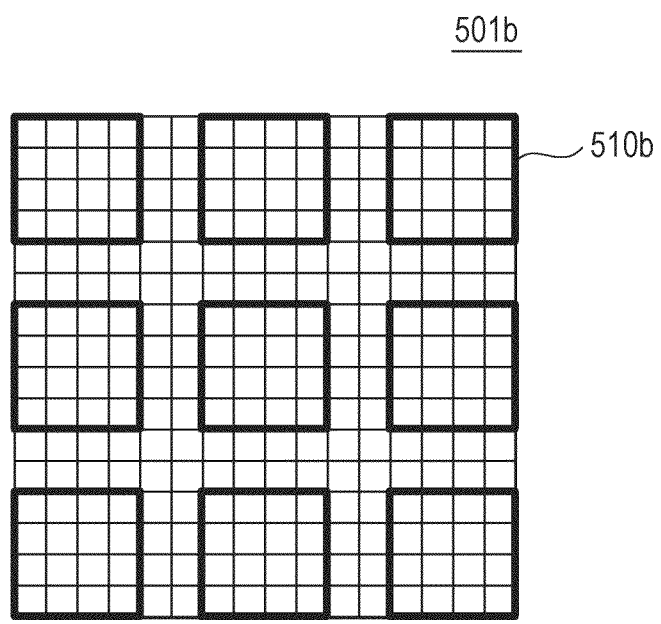
FIG. 5B illustrates another region division method example for the intensity distribution of a moire according to an embodiment of the present invention.

In step S421, the region is divided as illustrated in FIG. 5A or 5B in accordance with the number of region divisions determined in step S420. FIG. 5A illustrates squares enclosed by lines each indicating a pixel of the detector and squares enclosed by thick lines each indicating a divided region. Divided regions 510a are adjacent to each other within all regions 501a in the imaging range of a moire. In this case, one side of each region may be expressed by nq/m where the pixel pitch of the detector is q, the vertical and horizontal number of pixels is n, and the vertical and horizontal number of divisions is m. Here, m and n are integers. The way of division is not limited thereto. For example, as illustrated in FIG. 5B, the divided regions 510b are not adjacent to each other within all regions 501b of the imaging range of a moire. When the imaging range is divided as illustrated in FIG. 5B, some pixels are not contained in any regions.

Next, in step S430 and S431, the intensity information on the spectra corresponding to the carrier frequencies of the regions divided in step S421 is acquired.

In step S430, Fourier transform is performed on each of the divided regions. Because many diffracted light beams overlap and interfere when an interference pattern is formed, the carrier frequencies and their many harmonics component are included. However, because a moire has a form in which the carrier frequency components of the corresponding interference pattern are spatially enlarged, the moire may be expressed by Expression (2).

$$g(x,y)=a(x,y)+b(x,y)\cos(2\pi f_0 x+\phi(x,y)) \quad (2)$$

when a one-dimensional diffraction grating having the X-axis as the direction of period is used.

In this case, a(x,y) refers to the background, and b(x,y) refers to the amplitude of the carrier frequency component of the moire. $f_0$ refers to the carrier frequency of the moire, and $\phi(x,y)$ refers to the phase of the carrier frequency component. Expression (2) describes that a moire is expressed by the sum of the first term for the background and the second term having periodicity.

A moire generated when a two-dimensional diffraction grating is used, the carrier frequency component in the y-direction is superposed on Expression (2).

When the diffraction grating 130 is a π/2 diffraction grating having a checker pattern, the carrier frequency component is caused by the interference of 0-order diffracted light and +1-order diffracted light and interference of 0-order diffracted light and −1-order diffracted light. When the diffraction grating 130 is a π diffraction grating having a checker pattern, the carrier frequency component is caused by the interference of +1-order diffracted light and −1-order diffracted light.

In the 0-order diffracted light and 1-order diffracted light, the light beams at the positions away from the diffraction grating 130 by Nd overlap with each other. In the +1-order diffracted light and −1-order diffracted light, the light beams at the positions away from the diffraction grating 130 by 2Nd overlap with each other. In other words, these interferences are shearing interferences with a shear amount s of Nd when a π/2 diffraction grating is used and with a shear amount s of 2Nd when a π diffraction grating is used.

By the way, Expression (2) may be expressed as:

$$g(x,y)=a(x,y)+c(x,y)\exp(2\pi i f_0 x)+c^*(x,y)\exp(-2\pi i f_0 x) \quad (3)$$

$$\text{where } c(x,y)=\tfrac{1}{2}b(x,y)\exp[i\phi(x,y)] \quad (4).$$

Thus, the c(x,y) component or c*(x,y) component may be extracted from the interference fringe so that information on the phase $\phi(x,y)$ may be acquired.

In this case, Fourier transform on Expression (4) results in:

$$G(f_x,f_y)=A(f_x,f_y)+C(f_x-f_0,f_y)+C^*(f_x+f_0,f_y) \quad (5)$$

In this case, $G(f_x,f_y)$, $A(f_x,f_y)$, and $C(f_x,f_y)$ are two-dimensional Fourier transforms on g(x,y), a(x,y), and c(x,y).

Figure 6:
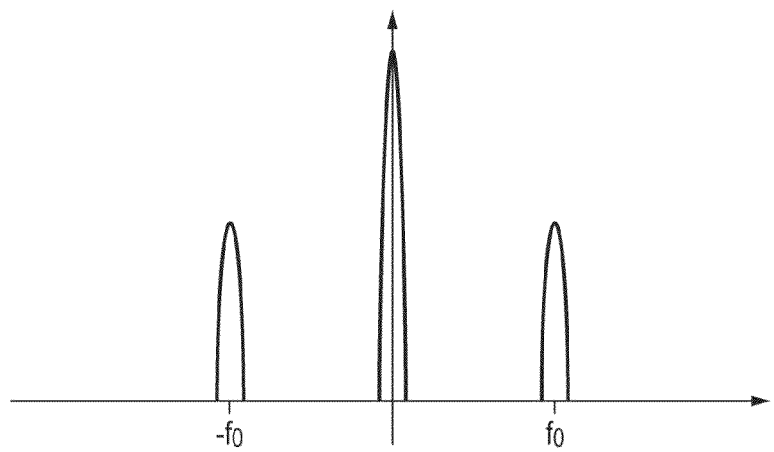
FIG. 6 illustrates a spatial frequency spectrum and spectra corresponding to the carrier frequencies according to an embodiment of the present invention.

FIG. 6 illustrates spatial frequency spectra acquired by performing Fourier transform on the intensity distribution of a moire detected when a grating having a one-dimensional period is used. Normally, three spectra occur as illustrated in FIG. 6. The center spectrum mainly originates in $A(f_x,f_y)$. On the other hand, the spectra on both sides correspond to the carrier frequencies originating in $C(f_x,f_y)$ and $C^*(f_x,f_y)$. These spectra have peaks at positions of $\pm f_0$.

In step S431, the intensity information on the spectra corresponding to the carrier frequencies are acquired. According to this embodiment, the intensity information on the spectrum corresponding to a carrier frequency may be a Carrier to Noise Ratio (hereinafter, called a CNR) that is a ratio between the peak intensity of spectrum corresponding to the carrier frequency and the intensity of the background noise around the spectrum. The CNR may be calculated by using the peak intensity of the spectrum corresponding to a carrier frequency and the intensity of the background noise in each of the regions divided in step S420. According to this embodiment, a CNR that is the intensity information on the spectrum corresponding to a carrier frequency is used to adjust the attitude of the diffraction grating or absorption grating. However, other values may be used to adjust the diffraction grating or absorption grating. The intensity information on the spectrum corresponding to a carrier frequency may be the peak intensity of the spectrum or the integrated intensity of the spectrum, for example. The peak intensity of a spectrum is the absolute value $|C(f_x,f_y)|$ or $|C^*(f_x,f_y)|$ of $C(f_x,f_y)$ or $C^*(f_x,f_y)$, and the integrated intensity of a spectrum is values of integral $\iint C(f_x,f_y)dxdy$ and $\iint C^*(f_x,f_y)dxdy$. The intensity information on the spectrum corresponding to a carrier frequency refers to information on an intensity of the spectrum ($C(f_x,f_y)$ or $C^*(f_x,f_y)$) corresponding to a carrier frequency and includes visibility. The visibility will be described according to a second embodiment.

Figure 7:
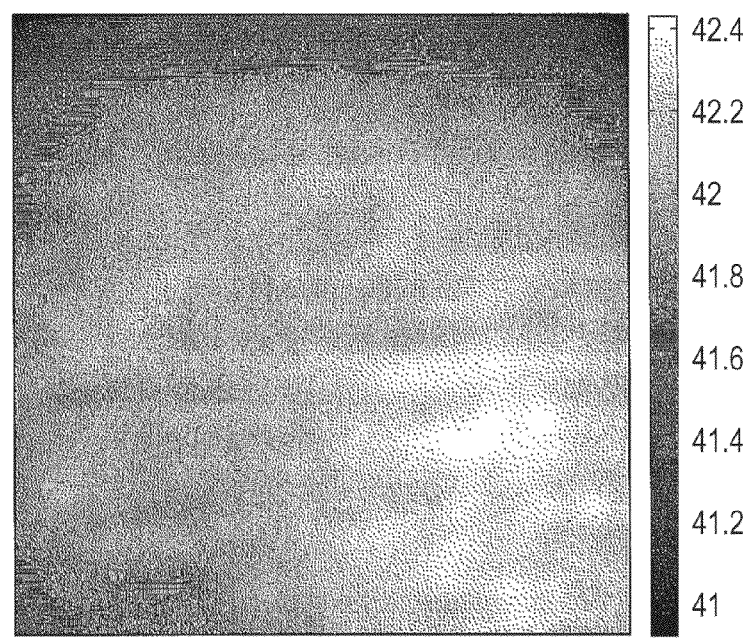
FIG. 7 illustrates a spectrum intensity distribution corresponding to carrier frequencies according to an embodiment of the present invention.

When the intensity information on the spectrum corresponding to a carrier frequency is a CNR, the attitude of the diffraction grating or absorption grating is adjusted on the basis of the CNR. Thus, a CNR of the entire imaging range may fall within a constant range even though the intensities of the background noise in the divided regions differ between regions. This results in reduction of the unevenness of image quality of the acquired phase image or differential image of a subject. In other words, it may prevent a specific region having high noise in the phase image or differential image. The different intensities of background noise between regions may be caused by the different period of the specific region of the diffraction grating or absorption grating due to a manufacturing error, for example. In the next step S440, the intensity distributions of the spectra are acquired from the intensity information of the spectra corresponding to the carrier frequencies acquired in step S430. The spectrum intensity distribution is generated for each of the regions divided in step S421. In other words, according to this embodiment, the CNR distribution is acquired from the CNR calculated in step S431. FIG. 7 illustrates an example of the spectrum intensity distribution, and the values of the CNRs calculated for the regions in step S431 are two-dimensionally mapped. However, the intensity distribution of a spectrum acquired in step S440 may not have a map form as illustrated in FIG. 7 in reality. The information from which the intensity information on the spectrum corresponding to a carrier frequency (CNR in this embodiment) of a plurality of regions may be identified is called a spectrum intensity distribution herein.

In step S441, the spectrum intensity distribution acquired in step S440 is analyzed about the vertical and horizontal directions of detector pixels, and the variation of the spectrum intensity distribution is evaluated on the basis of the standard deviation.

Next, in step S450, whether the standard deviation acquired in step S441 is equal to or higher than a threshold value δ0 or not is determined. If the acquired standard deviation is lower than δ0, the attitudes of the diffraction grating and absorption grating are not adjusted and are left as they are. If it is equal to or higher than δ0, the attitudes of the diffraction grating and absorption grating are adjusted as will be described below.

In step S441 and S450, the standard deviation is used to evaluate the variation of the spectrum intensity distribution and determine whether the attitudes of the diffraction grating and absorption grating are to be adjusted or not. However, the effect of the present invention may be acquired even by using values excluding the standard deviation for the determination on whether the adjustment is to be performed or not. For example, the absolute value of the difference between the maximum value and minimum value of the spectrum intensity information may be used to determine whether the adjustment is to be performed or not.

In step S460, the attitudes of the diffraction grating and absorption grating are adjusted such that the value of the region having a smaller value of the intensity information on the spectrum corresponding to a carrier frequency in the spectrum intensity distribution may be brought closer to the maximum value.

The adjustment of the attitudes of the diffraction grating and absorption grating will be described. In an imaging apparatus according to this embodiment, the attitudes of the diffraction grating and absorption grating are adjusted to adjust the inclinations of the diffraction grating and absorption grating about the light axis and the in-plane angle of the absorption grating against the interference pattern.

Figure 8A:
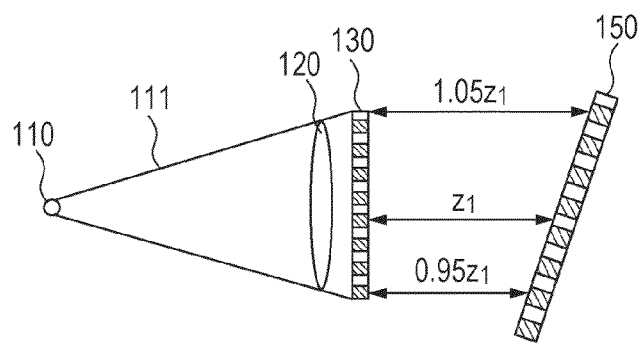
FIG. 8A illustrates the inclinations of a diffraction grating and an absorption grating about the light axis.

First, the adjustment of the inclinations of the diffraction grating and absorption grating about a light axis will be described. FIG. 8A illustrates a configuration example of an imaging apparatus to be used by X-ray Talbot interference. The absorption grating inclines about the light axis, the distances between the diffraction grating and the absorption grating (hereinafter, called an inter-grating distance) are larger in the upper part and are smaller in the lower part. The inclination about a light axis herein refers to a tilt about a light axis and indicates how much the diffraction grating or absorption grating inclines about the light axis. The distance between the centers of the diffraction grating and absorption grating is $z_1$ in Expression (1), the inter-grating distance at one point in the upper part is equal to $1.05\, z_1$, and the inter-grating distance at one point in the lower part is equal to $0.95\, z_1$.

Figure 8B:
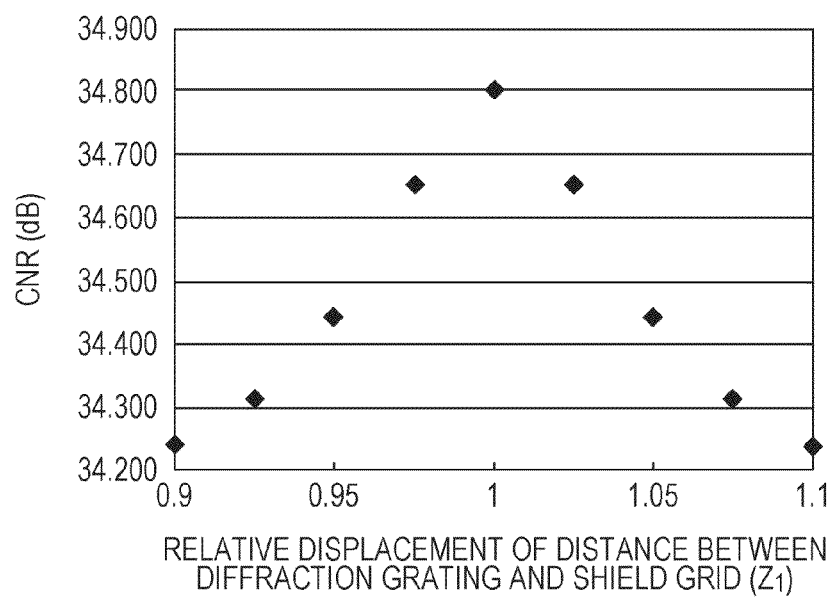
FIG. 8B illustrates changes in inter-grating distance and CNR.

FIG. 8B is a graph illustrating changes in CNR in accordance with the changes in inter-grating distance. The horizontal axis indicates the inter-grating distance when $z_1$ in Expression (1) is equal to 1, and the vertical axis indicates the CNR value. The graph illustrates that the displacement of the inter-grating distance of 5% from the distance ($z_1$) reduces the CNR by 0.35 dB.

The graph in FIG. 8B only illustrates the relationship between the inter-grating distance and the CNR. However, the spectrum intensity corresponding to a carrier frequency excluding the CNR such as the peak intensity of the spectrum and the integrated intensity of the spectrum also changes in accordance with the inter-grating distance. In this way, the inclinations of the diffraction grating and absorption grating about the light axis changes the intensity information on the spectrum corresponding to the carrier frequency. Thus, the inclinations of the diffraction grating and absorption grating about the light axis may be adjusted. A specific method example for adjusting the inclination of the diffraction grating and absorption grating about the light axis will be described. First of all, the intensity distribution of the spectrum acquired in step S440, differences between the CNR value of the region having the largest CNR and the CNR values of the other regions are calculated. After that, with reference to a graph as illustrated in FIG. 8B, the amount of adjustment for the inclinations of the diffraction grating or absorption grating about the light axis is calculated. On the basis of the calculation result, the inclination of the diffraction grating or absorption grating about the light axis is adjusted. Steps S410 to S450 are performed again. If the standard deviation of the spectrum intensity information corresponding to the carrier frequency is equal to or lower than the threshold value δ0, the adjustment on the attitudes of the diffraction grating and absorption grating about the light axis completes. Both of the inclinations of the diffraction grating and absorption grating may be adjusted. The direction of the adjustment on the inclination (about the X-ray source or the detector) is not available, the diffraction grating or absorption grating is inclined in an arbitrary direction, and step S410 to S431 are performed. The proper direction may be determined in accordance with the change in intensity information on the spectrum corresponding to a carrier frequency. The inclination of the diffraction grating or absorption grating about the light axis may be performed by one operation by omitting the determination on whether the standard deviation of the spectrum intensity information corresponding to the carrier frequency is equal to or lower than the threshold value δ0 (step S410 to S450).

According to another adjustment method example, the amount of adjustment on the inclination of the diffraction grating or absorption grating about the light axis may be adjusted without calculating the amount of adjustment on the inclination of the diffraction grating or absorption grating about the light axis.

According to this method, the amount of inclination movement may be predetermined, and the inclination of diffraction grating or absorption grating about the light axis is moved by the predetermined amount of movement. Then, step S410 to S450 are performed again. Until the standard deviation of the spectrum intensity information corresponding to the carrier frequency becomes equal to or lower than threshold value δ0, the inclination movement by the predetermined amount and step S410 to S460 may be repeated such that the attitude of the diffraction grating or absorption grating may be brought closer to a proper attitude.

Next, the adjustment of the in-plane angle of an absorption grating against an interference pattern will be described. The in-plane angle of the absorption grating against an interference pattern influences the period of a moire as described above and further influences the intensity information of the spectrum corresponding to the carrier frequency. An optimum in-plane angle is set in accordance with the pitches of the interference pattern and absorption grating. Different angles from the optimum in-plane angle produces smaller intensity information of the spectrum corresponding to the carrier frequency. For that, the rotation of at least one of the diffraction grating and absorption grating about the light axis may be adjusted to adjust the in-plane angle of the absorption grating against an interference pattern. The more specific adjustment method is the same as the method for adjusting the inclination of the diffraction grating and absorption grating about the light axis.

The rotation of the diffraction grating or absorption grating about the light axis is preferably adjusted such that the intensity information on the spectrum corresponding to the carrier frequency may be brought closer to the maximum value within the imaging range of the moire. On the other hand, the inclination of diffraction grating or absorption grating about the light axis may be adjusted to be closer to the minimum value, for example. In this case, after the inclination of diffraction grating or absorption grating about the light axis is adjusted, at least one of the distance from the X-ray source to the diffraction grating and the distance from the X-ray source to the absorption grating may be adjusted to bring the distance from the diffraction grating to the absorption grating closer to $z_1$ in Expression (1). Thus, the intensity information on the spectrum corresponding to the carrier frequency of the entire imaging range of a moire may increase, and the intensity information on the spectrum corresponding to the carrier frequency which is equivalent to or higher than that when the intensity information is brought closer to the maximum value.

The attitude of the diffraction grating or absorption grating may be adjusted automatically by using an actuator or manually by using a button for adjusting the attitude of the corresponding grating.

Second Embodiment

According to this embodiment, a visibility is used as the intensity information on the spectrum corresponding to a carrier frequency to adjust the attitude of at least one of a diffraction grating and an absorption grating. This embodiment will be described below with reference to FIG. 4, FIG. 6, FIG. 9, and FIG. 10. The descriptions on the parts overlapping with the first embodiment will be omitted.

The configuration of this embodiment is the same as the first embodiment illustrated in FIG. 1 except for the adjusting method with an adjusting unit. The description on the parts excluding the adjusting unit will be omitted.

The adjusting unit of this embodiment also divides the intensity distribution of a moire captured by a detector into a plurality of regions, calculates the spectrum intensity information corresponding to the carrier frequencies of the regions, and adjusts the attitudes of the diffraction grating and absorption grating on the basis of the distribution of the intensity information. However, according to this embodiment, a visibility is calculated in step S431 instead of a CNR.

The visibility refers to an indicator describing the contrast of a moire as described above. The visibility V of a one-dimensional moire is defined by Expression (6).

$$V = (I\max - I\min)/(I\max + I\min) \quad (6)$$

In this case, Imax is a maximum value of the intensity of the moire, and Imin is a minimum value of the intensity of the moire. According to this embodiment, a two-dimensional grating is used, and the moire intensity distribution is also two-dimensional. Thus, the direct use of the definition of the visibility described in Expression (6) is difficult. Accordingly, focusing on that Expression (6) is equal to the proportion of the amplitude of the sine waves to the average value for the profile having a sine-wave pattern, the visibility V is defined as Expression (7).

$$V = PC(f_x, f_y)/PA(f_x, f_y) \quad (7)$$

where $PC(f_x, f_y)$ is the peak value of a spectrum $C(f_x, f_y)$ corresponding to a carrier frequency, and $PA(f_x, f_y)$ is the peak value of a spectrum $A(f_x, f_y)$ corresponding to a DC component. The visibility is calculated by using the peak value of the spectrum corresponding to the carrier frequency and the peak value of the spectrum corresponding to the DC component in each of the regions divided in step S420. The use of visibility allows adjustment of the attitude of the diffraction grating or absorption grating on the basis of the visibility. Thus, the visibility of the entire imaging range may fall within a constant range even though the intensities of the background noise in the divided regions differ between regions. This results in reduction of the unevenness of image quality of the acquired phase image or differential image of a subject.

Figure 9:
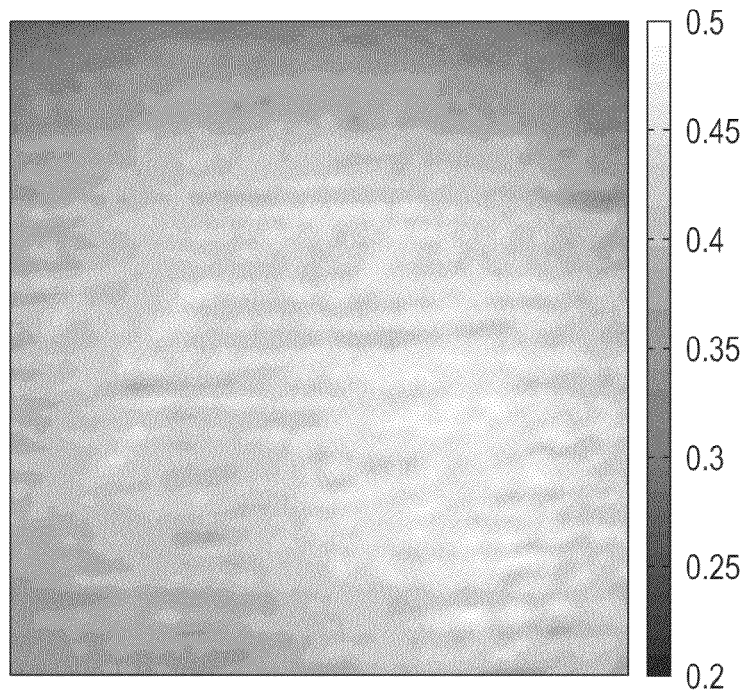
FIG. 9 illustrates a visibility distribution according to an embodiment of the present invention.

Next, like the first embodiment, in step S440, a visibility distribution is acquired from the value of the visibility acquired in step S431. The visibility distribution is generated for each of the regions divided in step S421, like the first embodiment. FIG. 9 illustrates an example of the visibility distribution acquired in step S440, and the values of the visibilities calculated for the regions in step S431 are two-dimensionally mapped. The visibility distribution acquired in step S440 may not have a map form as illustrated in FIG. 9 if it is information from which the numerical value information on visibilities for a plurality of regions may be identified. Like the first embodiment in which a CNR distribution is used to adjust the attitude of the diffraction grating or absorption grating, the visibility distribution is used to adjust the attitude of the diffraction grating or absorption grating in this embodiment.

In step S441, the visibility distribution acquired in step S440 is analyzed about the vertical and horizontal directions of detector pixels, and the variation of the visibility distribution is evaluated on the basis of the standard deviation.

Next, in step S450, whether the standard deviation acquired in step S441 is equal to or higher than a threshold value δ0 or not is determined. If the acquired standard deviation is lower than δ0, the attitudes of the diffraction grating and absorption grating are not adjusted and are left as they are. If it is equal to or higher than δ0, the attitudes of the diffraction grating and absorption grating are adjusted as will be described below.

According to this embodiment, the standard deviation is used to evaluate the variation of the visibility of each of the regions and determine whether the attitudes of the diffraction grating and absorption grating are to be adjusted or not. However, like the first embodiment, values excluding the standard deviation may be used for the determination on whether the adjustment is to be performed or not. For example, the absolute value of the difference between the maximum value and minimum value of the visibility may be used to determine whether the adjustment is to be performed or not.

In step S460, the attitudes of the diffraction grating and absorption grating are adjusted such that the value of the region having a smaller value of the visibility in the visibility distribution may be brought closer to the maximum value.

The method for adjusting the attitude of the diffraction grating or absorption grating is the same as the one in first embodiment.

Figure 10:
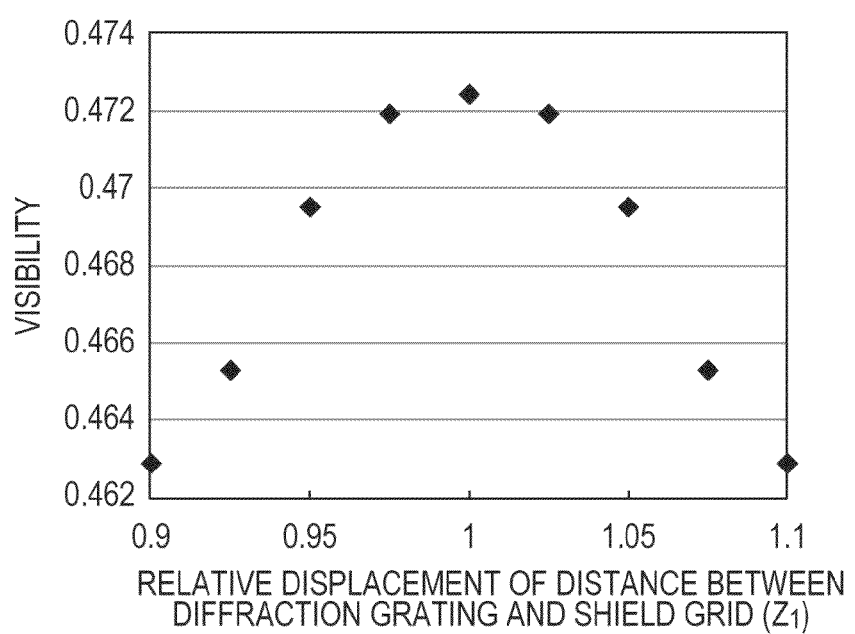
FIG. 10 illustrates changes in inter-grating distance and visibility value.

FIG. 10 is a graph illustrating changes in visibility in accordance with the changes in inter-grating distance. The horizontal axis indicates the inter-grating distance when $z_1$ in Expression (1) is equal to 1, and the vertical axis indicates the visibility value. As illustrated in FIG. 8A, when the absorption grating inclines about the light axis, the inter-grating distance varies, and the visibility thus varies. Accordingly, with reference to a graph as illustrated in FIG. 10, the amount of adjustment for the inclinations of the diffraction grating or absorption grating about the light axis is calculated. Thus, the attitude of the diffraction grating or absorption grating against the light axis is adjusted.

Steps S410 to S441 are performed again. If the standard deviation of the visibility value is equal to or lower than the threshold value δ0, the alignment adjustment completes. If the direction of the inclination adjustment is not available, the diffraction grating or absorption grating is moved in an arbitrary direction, and the proper direction may be determined in accordance with the change in visibility value caused by the movement of the grating.

According to another method example for adjusting the attitude of the diffraction grating or absorption grating, the inclination of the diffraction grating or absorption grating about the light axis is adjusted without calculating the inclination of diffraction grating or absorption grating about the light axis. According to this method, the average value of the visibility values is calculated, and the inclinations of the diffraction grating and absorption grating are adjusted by a predetermined amount of movement to adjust the distance between diffraction grating and absorption grating in the region having a different value from the average value. Until the standard deviation of the visibility value becomes equal to or lower than the threshold value δ0, steps S410 to S460 may be repeated such that the attitude of the diffraction grating or absorption grating may be brought closer to a proper attitude.

The adjustment of the in-plane angle of an absorption grating against an interference pattern is performed in the same manner as the first embodiment. The in-plane angle of the absorption grating against an interference pattern also influences the visibility value. An optimum in-plane angle is set in accordance with the pitches of the interference pattern and absorption grating. Different angles from the optimum in-plane angle produces a smaller visibility value. For that, the rotation of at least one of the diffraction grating and absorption grating about the light axis may be adjusted to adjust the in-plane angle of the absorption grating against an interference pattern. The more specific adjustment method is the same as the method for adjusting the inclination of the diffraction grating and absorption grating about the light axis.

The rotation of the diffraction grating or absorption grating about the light axis is preferably adjusted such that the visibility value may be brought into the maximum value within the imaging range of the moire. However, the inclination about the light axis may be adjusted to be brought closer to the minimum value, for example. In this case, after the inclination about the light axis is adjusted, the distance from the X-ray source to the diffraction grating and/or the distance from the X-ray source to the absorption grating may be adjusted to bring the distance from the diffraction grating to the absorption grating closer to $z_1$ in Expression (1). Thus, the visibility value of the entire imaging range of a moire may increase, and the visibility which is equivalent to or higher than that when the visibility is brought closer to the maximum value.

According to the first and second embodiments, the intensity distribution of a moire is divided into a plurality of regions, and Fourier transform is performed on each of the regions. The values acquired by the Fourier transform on the regions are used to calculate the information on the spectrum intensity corresponding to the carrier frequencies. On the basis of the calculated values, the attitude of the diffraction grating or absorption grating is adjusted. However, the method for adjusting the attitude of the diffraction grating or absorption grating is not limited thereto. For example, fringe scanning may be performed to calculate the visibilities of the divided regions, and, on the basis of them, the attitude of the diffraction grating or absorption grating may be adjusted. Alternatively, the inclination about the light axis may be adjusted in accordance with the degree of blur of a moire without dividing the intensity distribution of a moire into a plurality of regions.

The adjusting unit 190 also computes for acquiring a differential image or phase image of a subject from the intensity distribution of the moire detected by the detector 170.

In order to acquire a differential image or phase image of a subject, the adjusting unit 190 first performs Fourier transform on the intensity distribution of a moire detected by the detector 170 to calculate the spatial frequency spectrum. Next, the adjusting unit 190 uses the spectrum corresponding to the carrier frequencies to perform phase recovery processing and thus acquire the differential image or phase image. According to this embodiment, the adjusting unit 190 computes for acquiring a differential image or phase image of a subject. However, a separate computing device may be provided for computing for acquiring a differential image or phase image of a subject.

A display unit may be connected to the adjusting unit 190 (or computing device) to implement an X-ray image system. However, an X-ray imaging apparatus which is capable of computing to acquire a phase image or differential image of a subject and a display unit which displays an image on the basis of the computing result are collectively called an X-ray image system herein.

Having described the embodiments of the present invention up to this point, the present invention is not limited to the embodiments but may be modified and changed variously without departing from the spirit and scope of the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

INDUSTRIAL APPLICABILITY

The present invention is applicable to a subject imaging apparatus which uses phase changes caused by the transmission of an X-ray through a subject.

REFERENCE SIGNS LIST

110 X-ray source
130 diffraction grating
150 absorption grating
170 detector
190 adjusting unit

The invention claimed is:

1. An imaging apparatus comprising:
a diffraction grating which diffracts electromagnetic waves from an electromagnetic wave source;
a shield grating which shields a part of the electromagnetic waves diffracted by the diffraction grating;
a detector which detects an intensity distribution of the electromagnetic waves through the shield grating; and
an adjusting unit which adjusts an attitude of at least one of the diffraction grating and the shield grating on the basis of the detection result by the detector,
wherein the adjusting unit:
obtains information on the intensity distribution detected by the detector; and
adjusts an inclination of at least one of the diffraction grating and the shield grating so as to reduce a variation in distance between the diffraction grating and the shield grating such that the intensity distribution detected by the detector is maintained within an imaging range.

2. The imaging apparatus according to claim 1,
the adjusting unit is configured to adjust the inclination of at least one of the diffraction grating and the shield grating so that a minimum value of information on a spectrum intensity corresponding to a carrier frequency of the intensity distribution is brought closer to a maximum value of the information on the spectrum intensity corresponding to the carrier frequency of the intensity distribution.

3. An imaging apparatus comprising:
a diffraction grating which diffracts electromagnetic waves from an electromagnetic wave source;
a shield grating which shields a part of the electromagnetic waves diffracted by the diffraction grating;
a detector which detects an intensity distribution of the electromagnetic waves through the shield grating; and
an adjusting unit which adjusts an inclination of at least one of the diffraction grating and the shield grating about a light axis of the electromagnetic waves on the basis of the intensity distribution detected by the detector,
wherein the adjusting unit:
obtains information on the intensity distribution detected by the detector;
divides the information on the intensity distribution detected into a plurality of regions;
obtains intensity information on the spectrum corresponding to a carrier frequency of the intensity distribution in each of the regions; and adjusts the inclination of at least one of the diffraction grating and the shield grating about the light axis on the basis of the intensity information on the spectrum corresponding to the carrier frequency in the plurality of regions.

4. The imaging apparatus according to claim 3, wherein the adjusting unit is configured to adjust the inclination of at least one of the diffraction grating and the shield grating about the light axis so that a standard deviation of the intensity information on the spectrum corresponding to the carrier frequency in the plurality of regions is equal to or smaller than a threshold value.

5. The imaging apparatus according to claim 3, wherein the adjusting unit is configured to obtain the intensity information on the spectrum corresponding to the carrier frequency in each of the regions a plurality of times, and to adjust the inclination of at least one of the diffraction grating and the shield grating about the light axis a plurality of times.

6. The imaging apparatus according to claim 3, wherein the adjusting unit is configured to obtain the intensity information on the spectrum corresponding to the carrier frequency in each of the divided regions by performing Fourier transform on the intensity information of each of the divided regions.

7. The imaging apparatus according to claim 3, wherein the intensity information on the spectrum corresponding to a carrier frequency is a ratio between the intensity of the spectrum corresponding to the carrier frequency and the intensity of background noise around the spectrum.

8. The imaging apparatus according to claim 3, wherein the intensity information on the spectrum corresponding to a carrier frequency is a visibility value which is ratio between the peak value of the spectrum corresponding to the carrier frequency and the peak value of the spectrum corresponding to a DC (direct current) component thereof.

* * * * *